(12) United States Patent
Tanaami et al.

(10) Patent No.: US 8,466,410 B2
(45) Date of Patent: Jun. 18, 2013

(54) METHOD FOR MEASURING FLUORESCENT LIGHT AMOUNT OR LIGHT ABSORPTION AMOUNT AND DEVICE FOR MEASURING THE SAME

(75) Inventors: Takeo Tanaami, Musashino (JP); Hidetoshi Aoki, Musashino (JP); Yumiko Sugiyama, Musashino (JP); Souichirou Shimoda, Musashino (JP); Muneki Araragi, Musashino (JP)

(73) Assignee: Yokogawa Electric Corporation, Tokyo (JP)

( * ) Notice: Subject to any disclaimer, the term of this patent is extended or adjusted under 35 U.S.C. 154(b) by 322 days.

(21) Appl. No.: 12/848,596

(22) Filed: Aug. 2, 2010

(65) Prior Publication Data

US 2011/0031410 A1 Feb. 10, 2011

(30) Foreign Application Priority Data

Aug. 6, 2009 (JP) ................................. 2009-183317

(51) Int. Cl.
  *G01D 18/00* (2006.01)
(52) U.S. Cl.
  USPC ...................................................... 250/252.1
(58) Field of Classification Search
  USPC ............ 250/216, 227.2, 271, 459.1; 356/432
  See application file for complete search history.

(56) References Cited

U.S. PATENT DOCUMENTS

2004/0113096 A1  6/2004  Tanaami et al.
2009/0201506 A1*  8/2009  Tanaami et al. ............... 356/434

FOREIGN PATENT DOCUMENTS

| EP | 1441218 A2 | 7/2004 |
|---|---|---|
| EP | 1767910 A2 | 3/2007 |
| JP | 05346390 A | 12/1993 |
| JP | 2002-181712 A | 6/2002 |
| JP | 2004-191232 A | 7/2004 |
| JP | 2004191232 A | 7/2004 |
| JP | 2004-333333 A | 11/2004 |
| JP | 2005091701 A | 4/2005 |

OTHER PUBLICATIONS

European Office Action corresponding to European Patent Application No. 10170178.7, dated Aug. 31, 2011.
Japanese Office Action corresponding to Japanese Patent Application No. 2009183317, dated May 6, 2011.

* cited by examiner

*Primary Examiner* — Michael G Lee
*Assistant Examiner* — Matthew Mikels
(74) *Attorney, Agent, or Firm* — Sughrue Mion, PLLC (57) ABSTRACT

A method for measuring a fluorescent light amount, whereby a specimen is irradiated with excitation light, and fluorescent light generated from the specimen is measured by a light-receiving element via of a receiving optical system, the method includes the steps of irradiating the specimen with excitation light having a light-amount value per specified unit area traceable to the national standard, and designated on the surface of the specimen beforehand, causing the light-receiving element to measure the fluorescent light generated from the specimen, and computing a fluorescent light-amount as measured by the light-receiving element of the receiving optical system on the basis of an excitation light-amount per the specified unit area, optical coefficients of the receiving optical system, and the acceptance coefficient of the light-receiving element, thereby working out a light amount value per the unit area traceable to the national standard.

12 Claims, 6 Drawing Sheets

METHOD FOR MEASURING FLUORESCENT LIGHT AMOUNT OR LIGHT ABSORPTION AMOUNT AND DEVICE FOR MEASURING THE SAME

FIELD OF THE INVENTION

The present invention relates to a fluorescent light amount measurement method for measuring an amount of fluorescent light generated from a specimen, or a light absorption amount measurement method for measuring an amount of light absorbed by the specimen, and a measuring device for carrying out the measurement methods, respectively.

More specifically, the present invention relates to the fluorescent light amount measurement method whereby excitation light irradiated to a specimen, for measurement of fluorescent light, is standardized to a value representing "an amount of light, per unit area traceable to the national standard, and designated" to thereby enable an amount of the fluorescent light generated from the specimen to be quantitatively measured in terms of "a light amount per unit area traceable to the national standard" in instead of a ratio (a ratio value) as in the past, and a measuring device for use in carrying out the method.

Similarly, the present invention relates to the light absorption amount measurement method whereby excitation light irradiated to a specimen, in measurement of absorbed light, is standardized to a value representing "an amount of light, per unit area traceable to the national standard, and designated" to thereby enable an amount of absorbed light to be absorbed by the specimen to be quantitatively measured in terms of "an amount of light, per unit area traceable to the national standard" in stead of a ratio (a ratio value) as in the past, and a measuring device for use in carrying out the method.

BACKGROUND OF THE INVENTION

A micro-array scanner is well known as a measuring device to read out a DNA micro-array. With the use of the micro-array scanner, a DNA micro-array is irradiated with a laser beam, and an image of the DNA micro-array is captured while scanning the image, whereupon fluorescent light distribution of a target molecular can be measured in the form of a two-dimensional image.

RELATED ART LITERATURE

Patent Document

[Patent Document 1] JP 2004-333333 A
[Patent Document 2] JP 2004-191232 A

SUMMARY OF THE INVENTION

With the micro-array scanner described as above, however, since the measurement is made while executing current amplification of fluorescent light generated from a specimen (a target molecular) by use of a PMT (photoamplifier), there are limitations to linearity of an acceptance means and stability of amplification factor, and it is difficult to have a highly accurate correlation thereof with an amount of excitation light irradiated to the specimen. For this reason, a measured amount of fluorescent light is generally expressed in terms of an optional unit. A measured amount of fluorescent light received by a photo-detector, such as PMT, and so forth, is to be referred to as "a readout value" hereinafter.

Further, under conditions for making measurements on excitation light, such as a laser beam, and so forth, calibration means are not available, so that it is not possible perform direct comparison between a plurality of measurements, and between readout values of respective measuring devices within the two-dimensional image where the fluorescent light distribution has been read although relative measurement is possible within one screen.

In general, a measuring device, such as the micro-array scanner, has no provision in connection with measurement accuracy and reproducibility, and there is no guaranty that readout values obtained upon measurement of identical samples will be identical to each other even with the use of a measuring device of the same model, manufactured by the same maker. In other words, there exists, by nature, an instrumental error.

Naturally, there is no guaranty that readout values obtained similarly upon measurement of identical samples will be identical to each other when the measurement is made with the use of respective measuring devices manufactured by different makers. That is, it is difficult to standardize measurement regardless of the maker of a measuring device. More specifically, an absolute unit system traceable to the national standard, capable of coping with voltage (V), length (m), and so forth, in electrical·machinery systems, has not been adopted.

For this reason, a relative measurement method has been adopted in the past, whereby a measurement is made on a standard substance (control substance) as a comparison target, concurrently with measurement on a sample, thereby detecting a ratio of a measured value of the standard substance to a measured value of the sample.

However, the relative measurement method using the standard substance has problems as follows:

1a) There exist limitations to standardization of measurements, owing to circulation of the standard substance.

1b) There occur an increase in operation time and operation cost, and measurement quality undergoes deterioration owing to instability of the standard substance.

Meanwhile, light uniform in light-amount value, such as excitation light, can be measured by a photo diode, or the like, so as to be traceable to the national standard, however, only data on a dimensionless point, other than an image, is obtained in this case.

In contrast, JP 2004-191232 A has disclosed a method for calibrating a luminance value of a camera to an optical power (W) according to the national standard. By so doing, a light-amount value of the optical power traceable to the national standard is obtained for every pixel of an image as photographed (hereinafter referred to as "image power meter"). That is, spatial distribution of a specimen can be measured.

However, disclosed herein is only a configuration of the light receiving side thereof, and a specific method for calibrating excitation light is not described. A computation formula concerning a measuring system is not disclosed either.

It is an object of the present invention to standardize excitation light irradiated to a specimen for measurement of fluorescent light to a value of "a light amount per unit area traceable to the national standard, and designated" to thereby quantitatively measure an amount of fluorescent light generated from the specimen as "a light-amount value per unit area traceable to the national standard" instead of in terms of a ratio (a ratio value) as in the past.

Another object of the present invention is similarly to standardize light irradiated to a specimen for measurement of absorbed light to a value of "a light amount per a designated unit area traceable to the national standard, and designated" to thereby quantitatively measure an amount of absorbed light to be absorbed by the specimen as "a light-amount value per a unit area traceable to the national standard" instead of in terms of a ratio (a ratio value) as in the past.

To be more specific, the following function effects can be attained.

(1) An evaluation on a fluorescent light amount, and a light absorption amount, the evaluation having thus far been possible only by relative comparison, is now made on the basis of an absolute value having a light-amount (W) unit traceable to the national standard. By so doing, direct comparison is enabled between a plurality of measurements, and between the readout values of a plurality of measuring devices. As a result, standardization can be implemented.

(2) Once a relationship between the amount of a sample substance and a readout value can be decided upon with a measuring device, measurement of a sample is enabled without "preparation of a calibration curve according to the standard substance to be performed for correction of the measuring device on a measurement-by-measurement basis".

(3) With the use of a camera as a light-receiving element, a light-amount on a pixel-by-pixel basis can be obtained from not only a dimensionless point but also two-dimensional camera image itself, and every pixel of the image is displayed similarly in terms of the absolute value having the light-amount (W) unit traceable to the national standard, thereby enabling spatial distribution of a specimen to be quantitatively measured.

In accordance with one aspect of the present invention, there is provided a method for measuring a fluorescent light amount, whereby a specimen (a fluorescent molecule) is irradiated with excitation light, and fluorescent light generated from the specimen is measured by a light-receiving element via a receiving optical system, said method comprising the steps of: irradiating the specimen with excitation light having a light-amount value per specified unit area traceable to the national standard, and designated on the surface of the specimen beforehand, causing the light-receiving element to measure the fluorescent light generated from the specimen via the receiving optical system, and computing a fluorescent light-amount as measured by the light-receiving element via the receiving optical system on the basis of an excitation light-amount per the specified unit area, optical coefficients of the receiving optical system, and the acceptance coefficient of the light-receiving element, thereby working out a light amount value per the unit area traceable to the national standard.

With this method for measuring a fluorescent light amount, an amount of the fluorescent light generated from the specimen can be quantitatively measured as "a light amount per unit area traceable to the national standard", that is, as an output value of a unit system, for example, in terms of $(W/m^2)$, instead of a ratio (a ratio value) representing a ratio of an excitation light-amount to a fluorescent light-amount as in the past, Further, in accordance with another aspect of the present invention, there is provided a method for measuring a light absorption amount, whereby a specimen (a light-absorption molecule) is irradiated with irradiation light, and transmitted light undergoes absorption by the specimen to be measured by a light-receiving element via a receiving optical system, said method comprising the steps of: causing the light-receiving element to measure irradiation light at a light-amount value per specified unit area traceable to the national standard, and designated on the surface of the specimen beforehand via the receiving optical system; irradiating the specimen with the irradiation light; causing transmitted light undergoing absorption by the specimen to be measured by the light-receiving element via the receiving optical system; and computing a transmitted light amount measured by the light-receiving element on the basis of an irradiation light amount (a light-amount value prior to absorption) per the specified unit area traceable to the national standard, optical coefficients of the receiving optical system, and an acceptance coefficient of the light-receiving element, thereby working out a light absorption amount value per unit area traceable to the national standard.

According to this method for measuring a light absorption amount, an amount of light absorbed by a specimen can be quantitatively derived as "a light-amount per unit area traceable to the national standard" that is, as the output value of the unit system, for example, in terms of $(W/m^2)$, instead of in terms of the ratio value representing the ratio of an irradiation light amount to a light absorption amount as in the past.

In this case, the excitation light, or the irradiation light is set beforehand in terms of "a light-amount value per a specified unit area pre-designated". The excitation light, or the irradiation light is preset in terms of, for example, 1 $(W/m^2)$. Further, the optical coefficients of the receiving optical system, and the acceptance coefficient of the light-receiving element are instrumental factors inherent in a measuring device.

Meanwhile, in measurement of the fluorescent light, an amount of a fluorescent substance is expressed in terms of the ratio of the excitation light-amount to the fluorescent light-amount, whereas in measurement of the absorbed light, an amount of a light-absorbing substance is expressed in terms of the ratio of the irradiation light-amount to the light absorption amount.

Accordingly, in measurement of the fluorescent light, if the excitation light-amount is standardized, this will enable a measurement corresponding to the amount of the fluorescent substance to be made by simply measuring the fluorescent light-amount.

Further, in measurement of the absorbed light, if a transmitted light amount is measured, and the transmitted light amount is deducted from the irradiation light amount value pre-stored prior to the absorption, a light absorption amount of a molecule being measured can be worked out.

Accordingly, in measurement of absorbed light, a measurement corresponding to the amount of the light-absorbing substance can be made by simply standardizing the irradiation light amount to thereby measure a transmitted light amount, and executing computation with use of an irradiation light amount value pre-stored prior to the absorption.

Since in the conventional measurement of the fluorescent light, the amount of a fluorescent substance is expressed in terms of the ratio of the excitation light-amount to the fluorescent light-amount, and in the conventional measurement of the absorbed light, the amount of a light-absorbing substance is expressed in terms of the ratio of the irradiation light amount to the light absorption amount, the ratio being a dimensionless number, it has been impossible to make an evaluation in such a way as to be "traceable to the national standard".

However, if the evaluation is divided into two parts, that is, one for an excitation light system, and the other for a light-receiving system, this will enable calibration "traceable to the national standard", such as in terms of 1 $(W/m^2)$, and x $(W/m^2)$, respectively, and so forth. This is a point in the present proposition, for enabling standardization to be implemented by overcoming an instrumental error, and regardless of a difference in workmanship between makers.

That is, as described later in the present specification, accuracy of the excitation light amount or irradiation light amounts, expressed in terms of "per a specified unit area traceable to the national standard", respectively, can be ensured with the optical power meter, and so forth.

Furthermore, accuracy of the light-receiving element can be similarly ensured with the optical power meter and so forth.

In this case, even if the excitation light-amount is not expressed truly in terms of 1 (W/m$^2$), the readout value of a fluorescent light amount as received may be converted into "a standard excitation light amount" provided that it is within a range for precluding problems such as color fading, and saturation, occurring to fluorescent light, to be then corrected before being outputted.

If the excitation light is excessively intense against fluorescent light by, for example, 5%, the readout value is reduced by 5% while accurately correcting the zero point before outputting. Then, "a ratio", that is, the ratio of the excitation light amount to the fluorescent light amount, is properly kept, and the readout value comes to be a value equivalent to "an amount of a substance" in the case of the readout value being truly "a standard excitation light-amount", so that no problem occurs provided that precision is within allowance in standardization of the readout value.

Thus, if "a standard excitation light amount", or "a standard irradiation light amount" is preset as a rule, only a readout value corresponding to a received light amount can be standardized to be treated as a measured value corresponding to "an amount of a substance". This is a second point of the present invention.

In this case, decision on whether or not the readout value as standardized is to be directly related in value to molecularity, and number of moles, representing an actual amount of a substance, that is, whether or not calibration is to be made to an exact amount of a substance may be properly selected depending on an application.

Regardless of whether or not a micro-array scanner is used, for measurement of an amount (weight) of a substance on the basis of a fluorescent light amount, and a light absorption amount, a calibration curve is generally measured with the use of the standard substance in advance, and an actual amount of light obtained from a sample is applied to the calibration curve to thereby effect measurement of the amount of the substance.

Now, in the case of the measurement of the fluorescent light, the ratio of the excitation light amount to the fluorescent light amount corresponds to the amount of a fluorescent substance, whereas in the case of the measurement of the absorbed light, the ratio of the irradiation light amount to the light absorption amount corresponds to the amount of a light-absorbing substance.

Further, with physical and chemical appliances, in general, a state of a device, processing of a sample, and so forth is often corrected with the use of the standard substance for every measurement.

For example, in the case of measuring a constituent A in a sample of blood, determination on whether or not the blood is unsuitable for measurement owing to anemia or presence of a drug is made by making use of a constituent B suitable for stable measurement all the time. When variation in sample is corrected for with the use of an internal standard substance, as described above, such a standard substance is referred to as "an internal control" hereinafter.

Further, in the case where a sample is subjected to processing such as amplification, and filtering, if a substance C is mixed with the sample prior to the amplification, and an amount of the substance C after the processing is measured concurrently with measurement of the sample, this will render it to possible to check whether or not processing in-between has been executed with precision. When variation in sample processing is corrected for with the use of an external standard substance, as described above, such a standard substance is referred to as "an external control" hereinafter.

Further, in the case of a measuring device having instability, a fluorescent light amount standard substance is prepared, and an amount of light of the fluorescent light amount standard substance is measured prior to, or after measurement on a sample, thereby making correction on a light amount of the measuring device. In the case where variation in the light amount of the measuring device is corrected for with the use of the fluorescent light amount standard substance, as described above, such a standard substance is referred to as "a reference substance" hereinafter.

To sum up, it is evident that the standard substance has broadly two roles to play.

1) In the case of the measurement of the fluorescent light, to find out a corresponding factor between "a light amount ratio (ratio value)", expressed by the ratio of the excitation light amount to the fluorescent light amount, and "an amount of a substance" expressed by the amount of the fluorescent substance, and in the case of the measurement of the absorbed light, to find out a corresponding factor between "a light amount ratio (ratio value)", expressed by the ratio of the irradiation light amount to the light absorption amount, and "an amount of a substance" expressed by the amount of the light-absorbing substance.

2) To make correction on variation in sample, sample processing, or the light amount of a measuring device Further, an item under 2) as above can be considered to be divided into three sub-titles as follows:

2a) variation in sample is corrected for with the use of the internal standard substance (an internal control substance).

2b) variation in sample processing is corrected for with the use of the external standard substance (an external control substance).

2c) instability of a measuring device is corrected for with the use of the reference substance.

It is one object of the present invention to fulfill a function "instability of a measuring device is corrected for with the use of the reference substance" shown under sub-item 2c) as above. With a present-day measuring device for use in electrical and machinery sectors, correction for the instability of a measuring device on a measurement-by-measurement basis, with the use of the reference substance, has not been put into practice. Use of the reference substance will lead to an increase in operation time, and operation cost, and deterioration in measurement quality, due to instability of the reference substance, thereby rendering it difficult to standardize measurement. Therefore, it is preferable to be able to carry out accurate measurement without use of the reference substance.

Further, even when the internal control, and the external control have to be used because there exist variation in sample, and variation in sample processing, it is not possible to measure the variation in sample, and the variation in sample processing by use of a measuring device if the measuring device itself has instability.

In such a case, it will be impossible to obtain data necessary for effecting quality control of a sample, in a front-end process, quality control of the sample processing, or improvement on a sample processing process.

More specifically, if the measuring device can be stabilized, and the need for the reference substance can be eliminated, the following effects can be expected:

3a) the variation in sample can be measured with the use of the internal standard substance. As a result, such measured data as obtained can be put to use in the quality control of the sample in the next stage.

3b) the variation in sample processing can be measured with the use of the external standard substance. As a result, such measured data as obtained can be put to use in the quality control·improvement of the sample processing process in the next stage.

3c) an operation for correcting the light amount of the measuring device, executed with the use of the fluorescent light amount standard substance prior to, or after the measurement on the sample, is no longer required With the present invention, a calibration method has been devised, whereby the need for the reference substance can be eliminated, thereby rendering it possible to check whether or not the measuring device is stabilized. As a result, it has become possible to develop a stable measuring device, so that the effects described under items 3a) to 3c) as above can be expected by virtue of the stable measuring device, and the calibration method.

This means that the followings are enabled:

Cutback on correction with the use of the reference substance, as under item 2c) as above;

Reduction in the number of corrections·correction amount, with the use of the internal standard substance, by reducing the variation in sample, as under item 2a) as above; and Reduction in the number of corrections·correction amount, with the use of the external standard substance, by reducing the variation in sample processing, as under item 2b) as above.

Further, to find out the corresponding factor between "a light amount ratio (ratio value)", and "an amount of a substance", as described under item 1) as above, if the irradiation light amount, the light absorption amount, and so forth are expressed in terms of a value of the SI unit system, traceable to the national standard, as described later, it is possible to theoretically work out the corresponding factor between "a light amount ratio (ratio value)", and "an amount of a substance" on the basis of a light absorption amount, an absorption coefficient, various constants of a measuring device, and so forth. That is, if the absorption coefficient of a substance, under various conditions, the various constants of the measuring device, and so forth are known prior to measurement, there is no need for finding the corresponding factor between "a light amount ratio (ratio value)", and "an amount of a substance" on a measurement-by-measurement basis.

In general, the absorption coefficient of a substance is liable to a change according to temperature, pH, and so forth, however, once measurement is made on the absorption coefficient under new conditions, it is unnecessary to measure it again thereafter. Since "various constants of a measuring device" used to be instable, and have been susceptible to a change, re-calibration with the use of the standard substance has been required on a measurement-by-measurement basis.

With the measuring device according to the present invention, however, the excitation light side of the device and the light receiving side thereof are able to independently execute stable calibration in a manner traceable to the national standard. Accordingly, the various constants of the measuring device are stable, so that once a measurement is made under new conditions, there will arise no need for re-measurement thereof as long as precision is within allowance. This means reduction in the count of measurements to be made for finding the corresponding factor between "a light amount ratio (ratio value)", and "an amount of a substance", as described under 1) as above.

DETAILED DESCRIPTION OF THE PREFERRED EMBODIMENTS

Embodiments of a method for measuring an amount of fluorescent light, according to the present invention, are described hereinafter with reference to FIGS. 1 to 6, respectively.

First Embodiment

With the present embodiment, there is described an example in which a method for measuring a fluorescent light amount, according to the present invention, is applied to "measurement of molecularity distribution, according to a fluorescent light amount".

Figure 1:
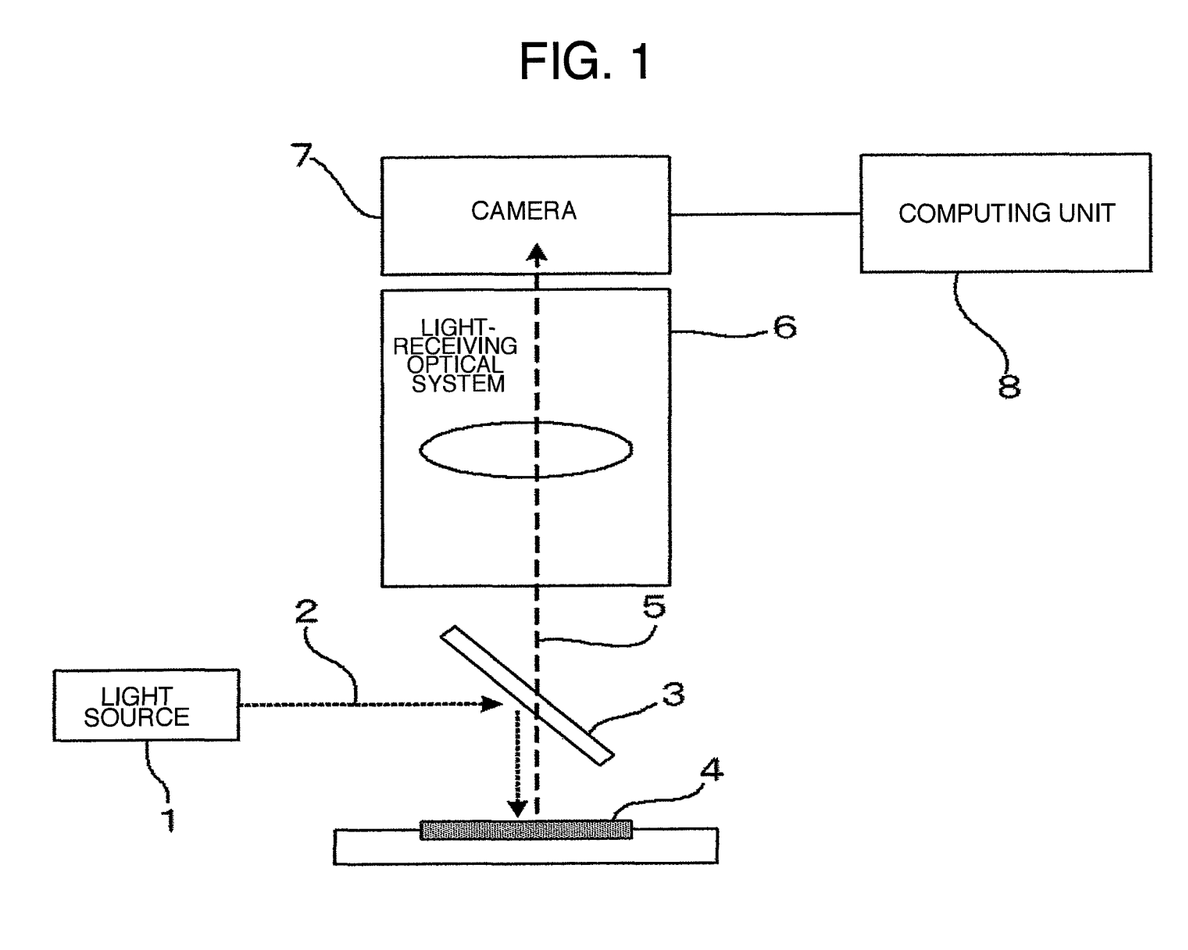
FIG. 1 is a block diagram showing a configuration of an optical layout of a specimen measurement system for use in measurement of molecularity distribution, to which a method for measuring a fluorescent light amount, according to the present invention, is applied, and so forth.

FIG. 1 is a block diagram showing a configuration of an optical layout of a specimen measurement device for use in fluorometry, and so forth.

As shown in FIG. 1, excitation light 2 from a light source 1 is reflected by a dichroic mirror 3 to irradiate the whole region of a specimen 4. Fluorescent light 5 from the specimen 4 is transmitted through the dichroic mirror 3 to fall on a light-receiving optical system 6 before forming an image of the specimen 4 on an image pickup plane of a camera 7. Further, a computing unit 8 for executing a series of processing (to be described later) is connected to the camera 7. The computing unit 8 acts as a theoretical light amount computing means, light amount measuring means, substance amount computing means, and molecularity computing means, respectively.

In the case where the method for measuring an amount of fluorescent light, according to the present invention, is applied to "a method for measuring the number of molecules according to an amount of fluorescent light" (fluorometry), an amount of fluorescent light on the specimen, and spatial distribution of molecularity can be measured by taking the following four steps in sequence. In this connection, "a measurement area" referred to hereunder indicates one unit area, such as one camera pixel, 1 μm$^2$, and so forth, in spatial measurement made in the direction perpendicular to the optical axis.

a) Measurements on a camera factor, and an amount (W/m$^2$) of excitation light to a specimen Measurements are made on a camera factor (W·s/m2/LSB) for use in the specimen measurement device, and an amount ($W/m^2$) of excitation light actually irradiated to a unit area of a specimen, thereby keeping the specimen measurement device ready for use.

b) Estimation on a theoretical monomolecular fluorescent light amount (W)

"A theoretical monomolecular fluorescent light amount (W) is estimated (calculated) according to molal absorptivity ε of a fluorescent molecule as a measurement target, quantum efficiency, excitation wavelength efficiency, and an amount ($W/m^2$) of excitation light.

c) Measurement on a fluorescent light amount (W) per the measurement area of a specimen "A fluorescent light amount (W) per the measurement area of a specimen" at a designated pixel is measured from a readout gradation value (LSB) of a pixel of a camera having actually picked up an image of the specimen, integrated time (s) for reading, and the camera factor ($W \cdot s/m^2/LSB$). The fluorescent light amount represents a value traceable to the national standard.

d) Determination of specimen molecularity per a measurement area

If "an amount (W) of fluorescent light, per the measurement area of a specimen" obtained by the step (c) as above is divided by "theoretical monomolecular fluorescent light amount (W)" as above, it is possible to determine (estimate) "specimen molecularity per the measurement area".

Figure 2A:
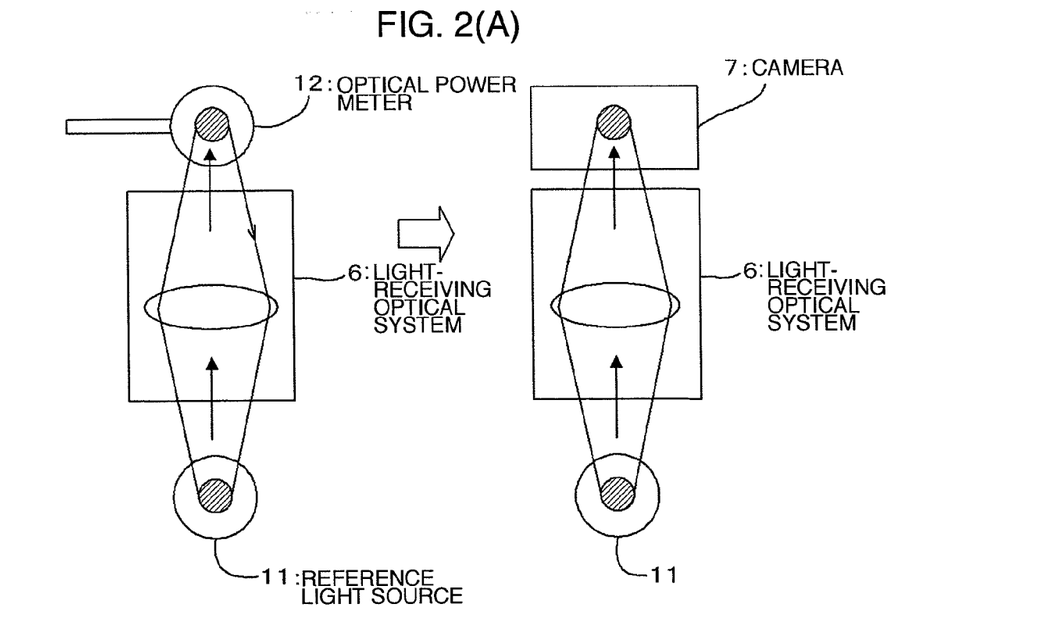
FIGS. 2(A) to 2(C) each are a view showing a procedure for calibration of a camera.
Figure 2B:
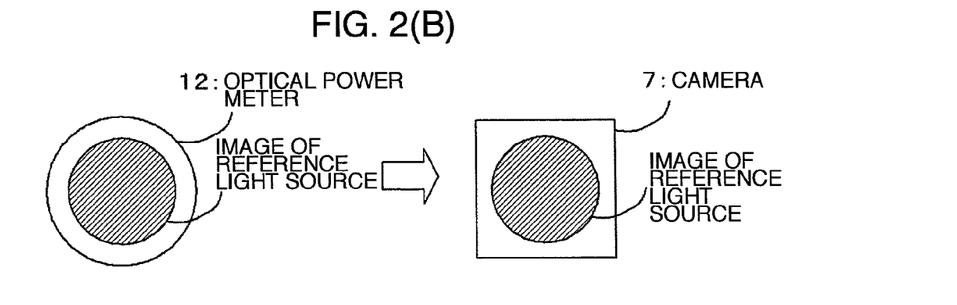
Figure 2C:
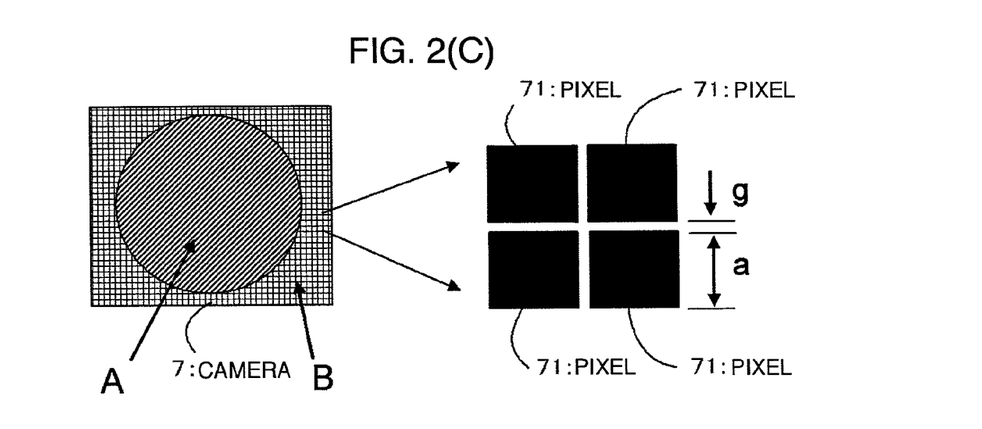

Specific operation contents in the case of fluorometry are described hereinafter.

a) Measurement on a camera factor, and an amount ($W/m^2$) of excitation light to a specimen Measurements are made on a camera factor ($W \cdot s/m2/LSB$) for use in the specimen measurement device, and an amount ($W/m^2$) of excitation light actually irradiated to a specimen, per a unit area of the specimen, thereby keeping the specimen measurement device ready for use.

a1) Determination on a camera factor Kc by calibration of a camera:

The camera factor Kc is a camera's intrinsic calibration value disclosed in JP 2004-191232 A, the value undergoing variation according to a measurement wavelength, but specific operation contents are not disclosed in JP 2004-191232 A. The camera factor Kc is found by the following method. FIGS. 2(A) to 2(C) each are a view showing a procedure for calibration of the camera.

a1.1) Calibration of a reference light-emitting source:

Measurements on an amount of light are made with a measuring device dedicated for use in measuring an amount of light (an optical power meter).

As shown in FIG. 2(A), first prepared is a reference light-emitting source 11 such as an LED, or a laser light source with stabilized optical power and wavelength, and so forth, and the whole amount of light from the reference light-emitting source 11 is caused to fall on an optical power meter 12 traceable to the national standard through a receiving optical system 6 to thereby measure a whole light amount Is1 (W=J/s).

a1.2) Calibration of a camera:

Subsequently, only the optical power meter 12 is replaced with a camera 7, and the whole amount of the light from the reference light source 11 is similarly caused to fall on the camera 7 through the receiving optical system 6. The readout value (gradation value) D (LSB) of the camera 7 is proportional to an incident light amount (W=J/s), and the integrated time t(s). Herein, the gradation value D is expressed by an integer multiple of LSB (Least Significant Bit: least significant digit at the time of A/D conversion), and in this case, 'LSB' is used as a gradation unit. All the gradation values of 16 bits are expressed by 0 to 65535 LSB. Further, there is the case where 'digit' is used as a gradation unit.

Since the readout value (gradation value) D (LSB) of the camera 7 is proportional to the incident light amount (W=J/s), as above, and the integrated time t(s), quotient obtained by dividing the total readout values D1 (LSB) of all light-receiving pixels by the integrated time t1(s) of the camera 7, will be proportional to the whole light amount Is1 (W) if gradation has no saturation. A conversion factor in this case is referred to as K1.

As the camera 7 is intended for acquisition of an image, all the pixels each have a conversion factor from a substantially identical incident light amount to gradation. The conversion factor K1 is substantially a mean value obtained by averaging out the conversion factors.

Accordingly, if a calibration operation is executed such that light evenly falls across the whole incident surface of the camera 7 when a total amount of light of a reference light-emitting source image falls on the camera 7, it is possible to obtain light from the reference light-emitting source as a whole even if uniformity is lacking in the amount of light provided that there is no saturation in gradation.

In this case, by taking advantage of the fact that the calibration operation itself makes use of pixels, pixels having a gradation value at zero can be excluded from pixels that are not irradiated with the light. For example, when a chip face of the camera 7 is irradiated with a light beam A as shown in FIG. 2(C), and if a region B is not irradiated with a light beam, having a gradation value at zero, calibration is executed by excluding a group of pixels in the region B.

Further, even in the case where pixels at the center are intense in gradation, and pixels on the periphery have a gradation value close to zero, linearity is maintained provided that there is no saturation, so that the factor hardly changes.

In general, the camera 7 has performance that it is used at resolution corresponding to 8 to 16 bits, ensuring uniformity of the respective pixels thereof. It is therefore considered that if the factor K1 can be confirmed with not less than a half of all the pixels of the camera having the pixels in a range of from several tens to several millions, the remainder of those pixels have the same camera factor although this is dependent on final measurement accuracy. Further, "an area of the reference light-emitting source image falling on the camera 7", S1 ($m^2$), (to be described later) is computed from the pixels that are irradiated with light.

Furthermore, even in the case where a non-receiving part g exists between adjacent pixels 71 (receiving parts a) of the camera 7, as shown in FIGS. 2(B), 2(C), light losses due to presence of the respective non-receiving parts g can be calibrated as a portion of the conversion factor K1 by similarly causing light to evenly fall across the whole incident surface of the camera 7.

More specifically, the non-receiving part (gap) "g" for separation of the respective pixels 71 from each other is provided between the pixels on a light-receiving plane of the camera 7. A light beam for calibration is irradiated to the non-receiving part g as well. For example, as shown in FIG. 2(B), in the case where the receiving parts "a" come to represent virtually 90% of an area of the light-receiving plane, there is a concern that an error occurs to a first calibration value according to the optical power meter due to light losses.

However, a pixel size is generally in a range of several μm to several tens of μm, whereas a beam diameter is as large as several mm, which is close to the size of a chip area in whole. That is, in the case of this calibration method, both the receiving part of the pixel, and the non-receiving part will be almost evenly irradiated with a light beam at the time of calibration.

This is approximate to conditions under which a subject is actually measured with a camera.

More specifically, if light reception efficiency dependent on the receiving part "a", and the non-receiving part "g" is 90%, the efficiency will be concurrently calibrated in the form of efficiency multiplied by photoelectric conversion efficiency at the time of the calibration. That is, a light loss caused by the presence of the non-receiving part, owing to the gap between the adjacent pixels, and so forth will not cause an error in calibration.

$$Is1 = K1 \times D1/t1 \,(W=J/s)$$

Further, if magnitude (an area of a reference light-emitting source image falling on the camera 7) of the reference light-emitting source 11 is defined as $S1(m^2)$, an amount of light, P1, per unit area, can be defined by the following expression:

$$P1 = Is1/S1 \quad (W/m^2)$$
$$= K1 \times D1/t1/S1 \quad (LSB/s/m^2)$$

Herein, the camera factor Kc is defined by the following expression:

$$Kc = K1/S1 (W \cdot s/m^2/LSB)$$

Accordingly, if Kc is used, the expression as above is replaced with expression $P1 = Kc \times D1/t1 \,(W/m^2)$ The above is generalized as follows:

$$Px = Kc \times D/t (W/m^2) \quad (1)$$

Where Kc: camera factor ($W \cdot s/m^2/LSB$), t: integrated time (s) at the time of measurement, D: gradation value (LSB)

With the use of the expression (1) as above, the light-amount value traceable to the national standard can be obtained from the readout value of the camera 7. In this case, it is important to be able to obtain a value in terms of ($W/m^2$) instead of a simple value in terms of (W) as in the case of a common optical power meter.

Figure 3:
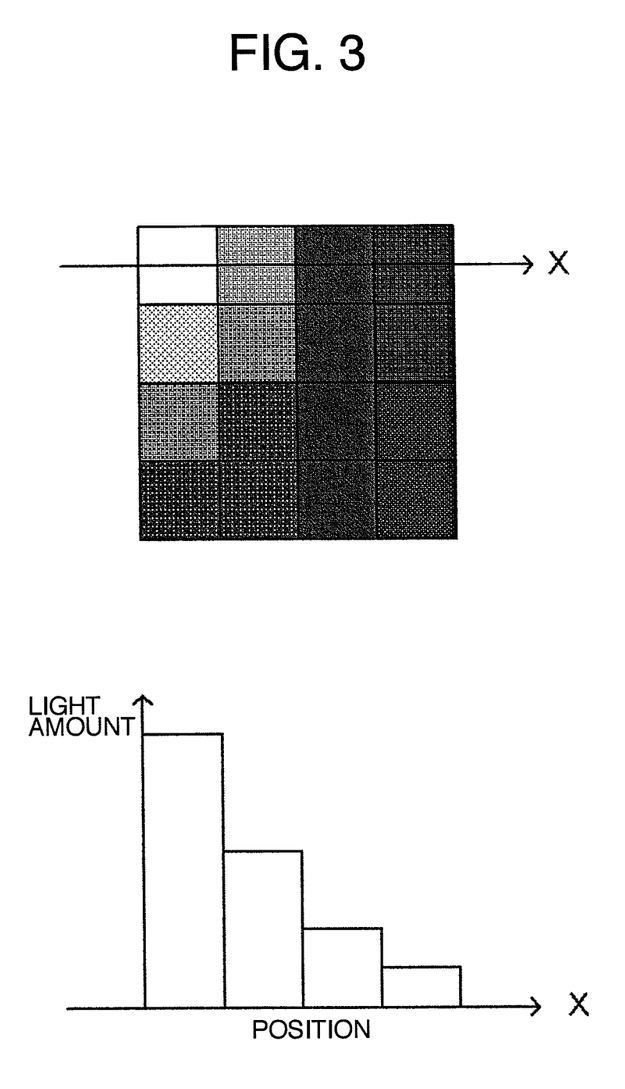
FIG. 3 shows an image that is read out with the camera by way of example.

FIG. 3 shows an image that is read out with a camera by way of example. When such an image as shown in FIG. 3 is obtained, (W) representing incident energy depends on how many photons have entered one pixel per unit time. In this case, one pixel length x(m) as well will be an important factor for determining the light-amount value.

That is, ($1/m^2$) of the camera factor Kc means that the present measurement makes use of not only a function of a camera, for measuring a light-amount value but also a function for measuring a length by the pixel.

Further, as described later in the present specification, in the case of carrying out "measurement on light amount distribution", it is necessary to introduce a concept of "a light amount value (W) per a measurement area (of a pixel, and so forth)" without fail. In such a case, if a value expressed in terms of ($W/m^2$), obtained from the camera factor Kc, corresponding to illuminance, is multiplied by the measurement area (the pixel area, and so forth), this will enable incident energy (W) that will actually fall onto one pixel to be computed.

a2) Measurement on excitation light

Measurements are carried out with the measuring device dedicated for use in measuring an amount of light (the optical power meter).

Figure 4:
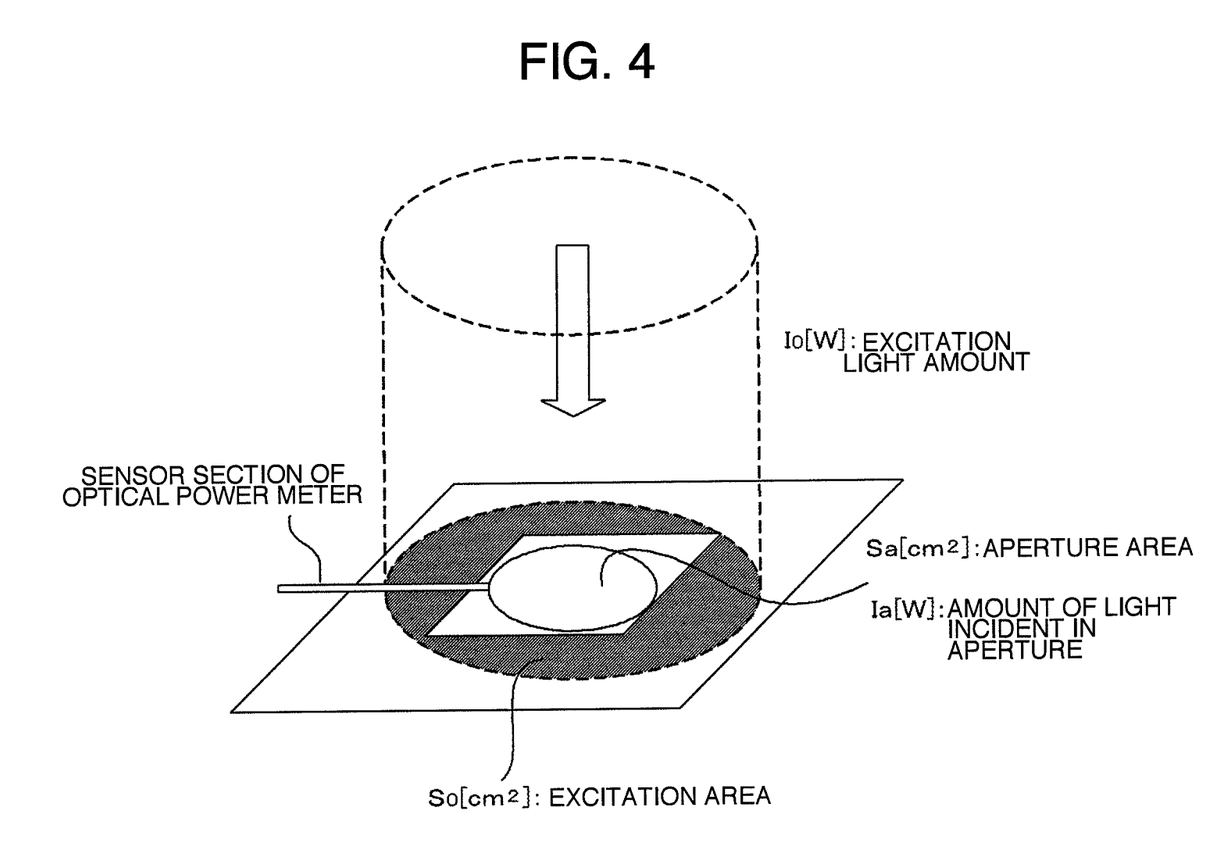
FIG. 4 is a view showing a concept of measurement on excitation light.

FIG. 4 is a view showing a concept of measurement on excitation light. The light-receiving part of the optical power meter is traceable to the national standard, making measurement on total light incident in an aperture of the entrance part thereof in terms of unit of (W). Accordingly, a measured light amount $I_o$ can be expressed as follows:

$$I_o = (S_o/S_a) \times I_a (W) \quad (2)$$

where $I_a$: an amount of light incident in an aperture (W), and $S_a$ = an aperture area ($cm^2$)

For accurate measurement, a measurement region of excitation light is preferably caused to coincide with a region for measurement as much as possible.

b) Estimation on a theoretical monomolecular amount (W) of fluorescent light, per a measurement area "A theoretical monomolecular amount (W) of fluorescent light", per a measurement area" is estimated (calculated) according to molal absorptivity c of a fluorescent molecule as a measurement target, quantum efficiency, excitation wavelength efficiency, and the amount ($W/m^2$) of excitation light.

Since a sufficiently diluted solution is used for normal fluorometry, $\epsilon CL \ll 1$ under conditions in this case, where $\epsilon$: molal absorptivity, C: molar concentration of a fluorescent molecule in the ground state, and L: an optical path length in a specimen b1) Estimation on a light absorption amount A light absorption amount is expressed as follows according to Lambert-Beer's laws:

$$\Delta I = 2.303 \times 10^3 \times \epsilon \times (I_o/S_o) \times n_o/N_A (W) \quad (3)$$

where $\Delta I$: light absorption amount (W), $\epsilon$: molal absorptivity ($M^{-1} cm^{-1} = L/mol/cm$) ... use is made of factors for a common logarithm, $I_o$: excitation light amount (W) @$S_o$, $S_o$: excitation area (cm2), $n_o$: the number of fluorescent molecules within an excitation area, $N_A$: Avogadro constant $6.0221415 \times 10^{23}$ Herein, a term "a measurement area" is introduced. The measurement area refers to the area of a region where molecularity is to be evaluated, such as the area of a camera pixel, an area expressed in units of 1 μm$^2$, and so forth. With the present measurement, the measurement area is expressed in units of ($m^2$), but may be expressed in terms of other units.

$S_m$: measurement area ($m^2$)

In the case of the present measurement, "fluorescent molecularity $n_m$" refers to the number of molecules per "a measurement area $S_m$".

$n_m$: the number of fluorescent molecules within a measurement area

Meanwhile, monomolecular absorptivity $\eta_a$ ($cm^2$) can be expressed as follows:

$$\eta_a = 22.303 \times 10^3 \times \epsilon/N_A (cm^2)$$

By replacing the expression (3) as above with $\eta_a$, the expression (3) becomes as follows:

$$\Delta I = \eta_a \times (I_o/S_o) \times n_o (W)$$

"A light absorption amount $\Delta Pa$ ($W/m^2$) per a measurement area, for $n_m$ pieces of fluorescent molecules" is obtained by replacing $n_o$ of the expression (3) with $n_m$ to be divided by the measurement area $S_m$.

$$\Delta Pa = \eta_a \times (I_o/S_o) \times (n_o/S_m)(W/m^2)$$

This demonstrates that the light absorption amount $\Delta Pa$ ($W/m^2$) and an mount of fluorescent light, per a measurement area, will vary depending on density ($n_o/S_m$) of fluorescent molecules, in the direction perpendicular to the optical axis, that is, whether one fluorescent molecule exists in 1 μm$^2$, or in 1 ($m^2$), and so forth, even if illuminance ($I_o/S_o$) ($W/m^2$) of excitation light remains constant.

If $n_m = 1$ without $S_m$, this means that only one molecule is assumed to exist in the whole region irradiated with the excitation light. In such a case, it will be impossible to ensure in which pixel of a camera picking up an image of pixels the image of the one molecule is picked up. For this reason, there is the need for defining theoretical molecularity on the basis of the number of molecules falling on one pixel. As shown in the expression (1), since the amount of light, Px, as computed by use of the camera factor Kc, is expressed in terms of (W/m$^2$), n$_m$ can be finally computed with ease by expressing the light absorption amount ΔPa as well in terms of (W/m$^2$).

b2) Estimation on an amount of fluorescent light

Figure 6:
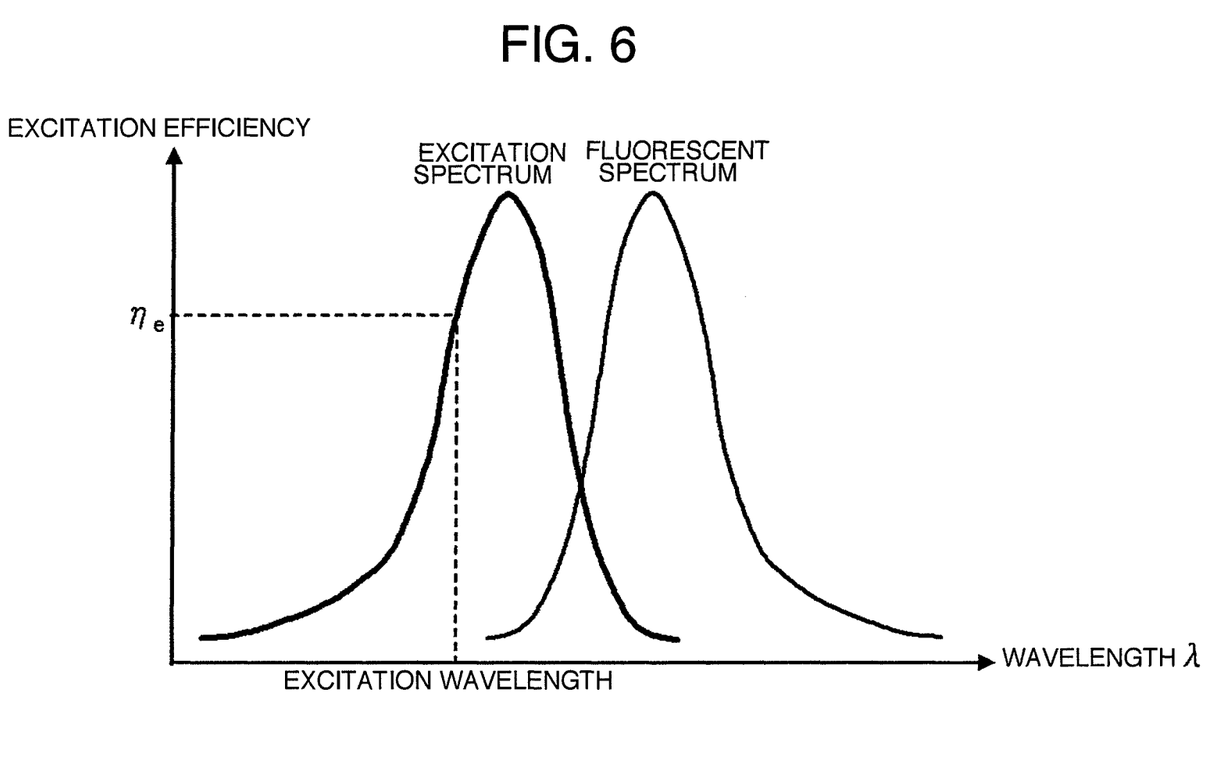
FIG. 6 is a view for illustrating excitation wavelength efficiency).

By adding quantum efficiency of fluorescent molecules, and so forth to the light absorption amount AP as above, a theoretical amount P$_f$ (W/m$^2$) of fluorescent light can be expressed by the following expression:

$$P_f = \Delta Pa \times \eta_q \times \eta_e \times \eta_t (W/m^2)$$

where $\eta_q$: quantum efficiency of a fluorescent molecule, $\eta_e$: excitation efficiency at a excitation wavelength of a fluorescent molecule (excitation wavelength efficiency) . . . refer to FIG. 6, and $\eta_t$: transmission efficiency of fluorescent wavelength of a light-receiving optical system A theoretical monomolecular fluorescent light amount I$_s$ in a measurement area is given as follows:

$$I_s = (\Delta I / n_o) \times \eta_q \times \eta_e \times \eta_t \quad (W) \quad (4)$$

$$= \eta_a \times \eta_q \times \eta_e \times \eta_t \times (I_o / S_o) \, (W)$$

c) Measurement on a fluorescent light amount (W) per the measurement area of a specimen "A fluorescent light amount (W) per the measurement area of a specimen" at a designated pixel is measured from a readout gradation value (LSB) of a pixel of a camera having actually picked up images of specimens, integrated time (s) for reading, and the camera factor (W·s/m$^2$/LSB).

By making use of the camera factor, a measured value P$_m$ (W/m$^2$) of fluorescent light from a specimen, per unit area, can be expressed as follows on the basis of the expression (4) as above:

$$P_m = Kc \times D/t (W/m^2)$$

Herein, (1/m$^2$) represents "a fluorescent light amount per unit area" according to distance measurement in a two-dimensional space using the pixels of a camera.

To convert "a fluorescent light amount per unit area" to "a measured fluorescent light-amount value I$_m$ (W) per a measurement area", it need only be sufficient to multiply the former by the measurement area S$_m$.

$$I_m = Kc \times D/t \times S_m (W) \quad (5)$$

where Kc: the camera factor (W·s/m$^2$/LSB), t: integrated time (s) at the time of measurement, and D; gradation value (LSB)

d) Measurement on the number of specimen molecules per a measurement area

The number of specimen molecules per a measurement area can be measured (estimated) by dividing "a fluorescent light amount (W) per the measurement area of a specimen" as under c) above by "a theoretical monomolecular amount (W) of fluorescent light" as under b) above.

"A theoretical monomolecular fluorescent light amount per a measurement area" is expressed by the expression (4)

$$I_s = \eta_a \times \eta_q \times \eta_e \times \eta_t \times (I_o / S_o)(W)$$

The measured fluorescent light-amount I$_m$ per the measurement area is found from the expression (5) as follows:

$$I_m = Kc \times D/t \times S_m (W)$$

Therefore, the number n$_m$ of fluorescent molecules as estimated can be expressed as follows:

$$n_m = I_m / I_s$$

$$= (Kc \times D/t) / \{\eta_a \times \eta_q \times \eta_e \times \eta_t \times (I_o / S_o) / S_m\}$$

$$= (Kc \times D \times S_o \times S_m) / (t \times \eta_a \times I_o \times \eta_q \times \eta_e \times \eta_t)$$

Further, in consideration of the measured value I$_o$ (W) of the excitation light amount, as expressed by the expression (2){I$_o$=(S$_o$/S$_a$)×I$_a$(W)}, the expression as above becomes as follows:

$$n_m = (Kc \times D \times S_o \times S_m) / (t \times \eta_a \times I_a \times \eta_q \times \eta_e \times \eta_t) \quad (6)$$

Now, both the camera factor Kc of a measuring device, and the transmission efficiency $\eta_t$ being intrinsic factors of the device, those can be integrated as the device constant "Ki".

$$Ki = Kc/\eta_t$$

Furthermore, a group of the factors in the case where a fluorescent reagent serving as a target is decided upon, including the aperture area S$_a$ for use in measurement on excitation light, can be integrated together as light-reception coefficient K$_a$ of excitation-light.

$$K_a = (Ki \times S_a)/(\eta_a \times \eta_q \times \eta_e)$$

In this case, the number n$_m$ of fluorescent molecules as estimated can be expressed in a simpler form as follows:

$$n_m = K_a \times D \times S_m / (I_a \times t)$$

Figure 5:
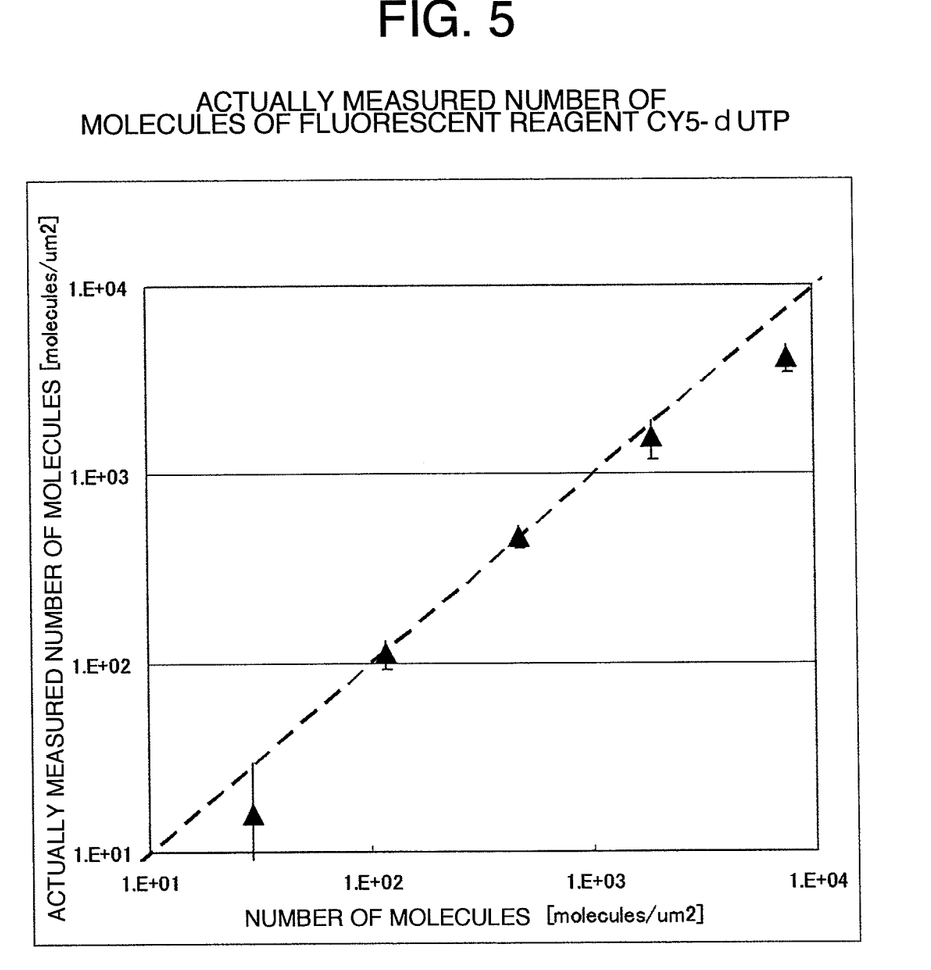
FIG. 5 is a graph showing measured number of molecules in the fluorescent reagent Cy5-dUTP.

FIG. 5 is a graph showing measured number of molecules in the fluorescent reagent Cy5-dUTP (manufactured by GE Health Care Corp.). In the figure, there is shown an example in which a glass substrate was spotted with UTP with addition of Cy5 varying in concentration, circular in shape, to thereby conduct fluorometry in accordance with a procedure described as above.

With the graph, an amount of fluorescent light in a spot-region was measured with a CCD camera, thence working out the number of molecules according to conversion formulas described in the foregoing, and the number of molecules, as the measured number of molecules, is plotted on the vertical axis while the number of fluorescent light molecules as spotted, computed from solution concentration in the spot-region on the substrate, a spot count, and a spot diameter, is plotted on the horizontal axis. In the graph, indicated by a broken line is a theoretical value at which the number of fluorescent light molecules as spotted is identical in value to the measured number of molecules.

It is evident from FIG. 5 that with the use of a method for measuring the number of molecules according to the present invention, the theoretical value is in good agreement with a measured value.

Only relative evaluation according to an optional unit system has so far been possible on a measured amount of fluorescent light, and so forth, whereas with the present invention, factors are integrated into the two intrinsic constants of a specimen measuring device, and one factor of an excitation (irradiation) light amount measuring device, as described hereunder, thereby enabling measurement of light-amount value to be carried out on the basis of an absolute value traceable to the national standard having a light-amount (W) unit. As a result, comparison between a plurality of measurements performed with the same measuring device over time, and comparison between dissimilar measuring devices are enabled.

The two intrinsic constants of the specimen measuring device are Kc: the camera factor, and $\eta_r$: the transmission efficiency of the fluorescent wavelength of the light-receiving optical system while the one factor of the excitation (irradiation) light amount measuring device is $S_a$: the aperture area (for measurement of an excitation light amount).

Further, it is possible to measure (estimate) the number of molecules present in a specimen on a measurement area-by-measurement area basis according to an amount of light (fluorescent light, emitted light, absorption light) from the specimen and a molecular constant.

More specifically, on the assumption that the theoretical monomolecular fluorescent light amount $I_s$ is given as follows:

$$I_s = \eta_a \times \eta_q \times \eta_e \times \eta_r \times (I_o/S_o)(W)$$

The measured value $P_m$ (W/m$^2$) of the fluorescent light from the specimen, per unit area, is as follows:

$$P_m = Kc \times D/t (W/m^2)$$

Or the measured fluorescent light-amount $I_m$ per the measurement area is as follows:

$$I_m = Kc \times D/t \times S_m (W)$$

Whereupon the number $n_m$ of fluorescent molecules within the measurement area ($S_m$) is expressed as follows:

$$n_m = (Kc \times D \times S_o \times S_m)/(t \times \eta_a \times I_o \times \eta_q \times \eta_e \times \eta_r)$$

Now, constants concerning fluorescent molecules (the fluorescent reagent), necessary for computation, are the following three factors:

$\epsilon$: molal absorptivity, $\eta_q$: quantum efficiency of a fluorescent molecule, and $\eta_e$: the excitation wavelength efficiency at the excitation wavelength of a fluorescent molecule Further, if the present invention is applied to a two-dimensional image, this will enable not only information on a point in O-dimension but also an amount of light per each pixel from a camera image itself in two-dimensions, so that it is possible to measure two-dimensional spatial distribution of fluorescent molecules over the specimen. If the present invention is applied to, for example, the method disclosed in JP 2004-191232 A, the two-dimensional spatial distribution of the fluorescent molecules over the specimen can be measured.

Furthermore, if the present invention is combined with a confocal optical system instead of with a common microscope, or camera, this will render it possible to measure not only two-dimensional but also even three-dimensional spatial distribution of the fluorescent molecules.

Now, application examples of the invention, concerning fluorescent light, include the following:

(1) With a DNA micro-array having a nucleic acid immobilized on a substrate, fluorescent molecularity of the nucleic acid after hybridization can be worked out. Then, if one fluorescent molecule is bonded to one molecule of the nucleic acid as a target to be hybridized, it is possible to find out molecularity of the hybridized nucleic acid as the target.

(2) By converting a signal after hybridization (hereinafter referred to as "hybri") of a DNA micro-array into an amount (W) of light, comparison of hybri-result can be made between different platforms.

(3) If fluorescent molecules identical in numbers to probe nucleic acids spotted on a measurement substrate, or nucleic acid molecules with a known fluorescent molecularity per molecule are kept separately immobilized on the substrate, this will render it possible to find out hybri-effects. This is particularly useful for correction when fading of fluorescence becomes a problem.

(4) If known fluorescent molecules are introduced in a reaction such as binding between a receptor and a ligand, in a cultured cell, protein migration on a filament in a cell, and so forth, the reaction in the cell can be quantitatively measured by counting the number of the molecules.

Second Embodiment

With the first embodiment, the fluorescent light is dealt with, however, the present invention can be applied to measurement of a light absorption amount, as well.

With the present invention, there is provided a method for measuring a light absorption amount, whereby a light-absorbing molecule is irradiated with irradiation light, and light absorbed by the light-absorbing molecule is measured by a light-receiving element via a receiving optical system, thereby measuring a light absorption amount of a specimen, said method comprising the steps of:

irradiating a sample with irradiation light at a light-amount value per specified unit area traceable to the national standard, and designated on the surface of the sample beforehand, causing the irradiation light to be absorbed by the light-absorbing molecule as the sample, causing transmitted light undergoing absorption by the sample to be measured by the light-receiving element via the receiving optical system, and computing a light absorption amount value per unit area traceable to the national standard from a transmitted light amount measured by the light-receiving element, and a light amount value pre-stored prior to absorption on the basis of an irradiation light amount per the specified unit area traceable to the national standard, optical coefficients of the receiving optical system, and the acceptance coefficient of the light-receiving element.

According to this method for measuring a light absorption amount, an amount of light absorbed by a specimen can be quantitatively derived in terms of "a light-amount per unit area traceable to the national standard" instead of in terms of a ratio value representing a ratio of an irradiation light amount to a light absorption amount.

In this case, the irradiation light is set beforehand in terms of "a light-amount value per a specified unit area pre-designated". The irradiation light is preset as "a standard irradiation light amount" in terms of 1 (W/m$^2$), and so forth. Further, the optical coefficients of the receiving optical system, and the acceptance coefficient of the light-receiving element are instrumental factors inherent in a measuring device.

Meanwhile, in measurement of absorbed light, an amount of a light-absorbing substance is expressed in terms of the ratio of the irradiation light amount to the light absorption amount.

Accordingly, in measurement of the absorbed light, if a transmitted light amount is measured, and the transmitted light amount is deducted from the light amount value pre-stored prior to the absorption, a light absorption amount of a molecule being measured can be worked out.

Accordingly, in measurement of absorbed light, a measurement corresponding to the amount of the light-absorbing substance can be made by simply standardizing the irradiation light amount to thereby measure a transmitted light amount, and executing computation with use of an irradiation light amount value pre-stored prior to the absorption.

This is a point of the present proposition.

In the case of the conventional measurement of the light absorption amount, the amount of a light-absorbing substance is expressed in terms of the ratio of the irradiation light amount to the transmitted light amount, the ratio being a dimensionless number, so that it has been impossible to make an evaluation that is "traceable to the national standard".

However, if the evaluation is divided into two parts, that is, one for an irradiation system, and the other for a light-receiving system, this will enable calibration "traceable to the national standard", such as in terms of $1(W/m^2)$, and x $(W/m^2)$, respectively, and so forth. This is a point in the present proposition, for enabling standardization to be implemented by overcoming an instrumental error, and regardless of a difference in workmanship between makers.

That is, as described above, accuracy of the irradiation light amounts, expressed in terms of "per a specified unit area traceable to the national standard", respectively, can be ensured with the optical power meter, and so forth.

Furthermore, accuracy of the light-receiving element can be similarly ensured with the optical power meter and so forth.

As described in the foregoing, with the method for measuring a fluorescent light amount or a light absorption amount, according to the present invention, molal absorptivity E of a specimen and excitation wavelength efficiency $\eta_e$ can be directly derived from the light amount of a specimen, molecularity thereof being measured, on the basis of a ratio of a measured light amount of the specimen to a theoretical light amount as computed.

Having described the embodiments of the invention in the foregoing, it is to be understood that an application range of the present invention be not limited thereto, and that the present invention may be widely applied to methods for measuring the number of molecules for quantitatively measuring the molecularity of a specimen, on the basis of a light amount having a correlation with the molecularity.

What is claimed is:

1. A method for measuring a fluorescent light amount, whereby a specimen is irradiated with excitation light, and fluorescent light generated from the specimen is measured by a light-receiving element via a receiving optical system, said method comprising:
   a step of acquiring a relationship between a light-amount value of the fluorescent light generated from the specimen per unit area and an output value of the light-receiving element;
   a step of irradiating the specimen with excitation light having a light-amount value per specified unit area traceable to a national standard, and designated on a surface of the specimen beforehand;
   a step of acquiring the output value of the light-receiving element when the specimen is irradiated with the excitation light by the step of irradiation step; and
   a step of computing an absolute value of a ratio of a light-amount of the excitation light per unit area with which the specimen is irradiated to the light-amount value of fluorescent light generated from the specimen per specified unit area, or the number of molecules contained in the specimen per unit area, based on the relationship between the output value of the light-receiving element acquired by the step of acquiring the output value, and the relationship acquired by the step of acquire a relationship, and the light-amount value per specified unit area.

2. A method for measuring a light absorption amount, whereby a specimen is irradiated with irradiation light, and transmitted light undergoes absorption by the specimen to be measured by a light-receiving element via a receiving optical system, said method comprising:
   a step of acquiring a relationship between a light-amount value of transmitted light amount from the specimen per unit area and an output value of the light-receiving element;
   a step of irradiating the specimen with the irradiation light having a light-amount value per specified unit area traceable to a national standard, and designated on a surface of the specimen beforehand;
   a step of acquiring the output value of the light-receiving element when the specimen is irradiated with irradiation light by the irradiation step; and
   a step of computing an absolute value of a ratio of a light-amount of the irradiation light per unit area with which the specimen is irradiated to the light-amount value of transmitted light from the specimen per unit area, based on the relationship between the output value of the light-receiving element acquired by the step of acquiring the output value, and the relationship acquired by the step of acquire a relationship, and the light-amount value per specified unit area.

3. A device for measuring a fluorescent light amount, whereby a specimen is irradiated with excitation light, and fluorescent light generated from the specimen is measured by a light-receiving element via a receiving optical system, said device comprising:
   relationship acquisition means for acquiring a relationship between a light-amount value of fluorescent light generated from the specimen per unit area and an output value of the light-receiving element;
   light source means for irradiating the specimen with excitation light having a light-amount value per specified unit area traceable to a national standard, and designated on a surface of the specimen beforehand;
   output value acquisition means for acquiring the output value of the light-receiving element when the specimen is irradiated with the excitation light; and
   computing means for computing an absolute value of a ratio of a light-amount of the excitation light per unit area with which the specimen is irradiated to the light-amount value of fluorescent light generated from the specimen per specified unit area, or the number of molecules contained in the specimen per unit area, based on the relationship between the output value of the light-receiving element acquired by the output value acquisition means, the relationship acquired by the relationship acquisition means and the light-amount value per specified unit area.

4. A device for measuring a light absorption amount, whereby a specimen is irradiated with irradiation light, and transmitted light undergoes absorption by the specimen to be measured by a light-receiving element via a receiving optical system, said device comprising:
   relationship acquisition means for acquiring a relationship between a light-amount value of transmitted light amount from the specimen per unit area and an output value of the light-receiving element;
   light source means for irradiating the specimen with the irradiation light having a light-amount value per specified unit area traceable to a national standard, and designated on a surface of the specimen beforehand;
   output value acquisition means for acquiring the output value of the light-receiving element when the specimen is irradiated with irradiation light by the light source means; and
   computing means for computing an absolute value of a ratio of a light-amount of the irradiation light per unit area with which the specimen is irradiated to the light-amount value of transmitted light from the specimen per unit area, based on the relationship between the output value of the light-receiving element acquired by the output value acquisition means, and the relationship acquired by relationship acquisition means, and the light-amount value per specified unit area.

5. The method for measuring the fluorescent light amount of claim 1, further comprising a step of calibrating a camera having pixels,
wherein the calibrating of the camera comprises excluding pixels having zero gradation value.

6. The method for measuring the fluorescent light amount of claim 1,
further comprising a step of estimating a theoretical monomolecular amount of the fluorescent light,
wherein a sufficiently diluted solution is used in the estimating the theoretical monomolecular amount of the fluorescent light such that a condition, $\epsilon CL \ll 1$, is satisfied where
$\epsilon$ is molal absorptivity, C is molar concentration of a fluorescent molecule in the ground state, and L is an optical path length in a specimen.

7. The method for measuring the light absorption amount of claim 2, further comprising a step of calibrating a camera having pixels,
wherein the calibrating of the camera comprises excluding pixels having zero gradation value.

8. The method for measuring the light absorption amount of claim 2,
further comprising a step of estimating a theoretical monomolecular amount of the fluorescent light,
wherein a sufficiently diluted solution is used in the estimating the theoretical monomolecular amount of the fluorescent light such that a condition, $\epsilon CL \ll 1$, is satisfied where
$\epsilon$ is molal absorptivity, C is molar concentration of a fluorescent molecule in the ground state, and L is an optical path length in a specimen.

9. The device for measuring the fluorescent light amount of claim 3, further comprising a camera calibration unit which calibrates a camera having pixels,
wherein the camera calibration unit excludes pixels having zero gradation value.

10. The device for measuring the fluorescent light amount of claim 3, further comprising a monomolecular amount estimating unit which estimates a theoretical monomolecular amount of the fluorescent light,
wherein the monomolecular amount estimating unit uses a sufficiently diluted solution in such that a condition, $\epsilon CL \ll 1$, is satisfied where
$\epsilon$ is molal absorptivity, C is molar concentration of a fluorescent molecule in the ground state, and L is an optical path length in a specimen.

11. The device for measuring the light absorption amount of claim 4, further comprising a camera calibration unit which calibrates a camera having pixels,
wherein the camera calibration unit excludes pixels having zero gradation value.

12. The device for measuring the light absorption amount of claim 4, further comprising a monomolecular amount estimating unit which estimates a theoretical monomolecular amount of the fluorescent light,
wherein the monomolecular amount estimating unit uses a sufficiently diluted solution in such that a condition, $\epsilon CL \ll 1$, is satisfied where
$\epsilon$ is molal absorptivity, C is molar concentration of a fluorescent molecule in the ground state, and L is an optical path length in a specimen.

* * * * *